US008833631B2

(12) United States Patent
Munro, III et al.

(10) Patent No.: US 8,833,631 B2
(45) Date of Patent: Sep. 16, 2014

(54) DELIVERY APPLICATOR FOR RADIOACTIVE STAPLES FOR BRACHYTHERAPY MEDICAL TREATMENT

(76) Inventors: John J. Munro, III, North Andover, MA (US); Kevin Schehr, New Orleans, LA (US); Krissie K. Zambrano, New Orleans, LA (US); Matthew Hollows, Westminster, MA (US)

(*) Notice: Subject to any disclaimer, the term of this patent is extended or adjusted under 35 U.S.C. 154(b) by 599 days.

(21) Appl. No.: 13/108,759

(22) Filed: May 16, 2011

(65) Prior Publication Data

US 2012/0292369 A1 Nov. 22, 2012

(51) Int. Cl.
*A61B 17/068* (2006.01)
*A61K 51/12* (2006.01)
*A61B 17/072* (2006.01)
*A61B 17/00* (2006.01)
*A61B 17/29* (2006.01)
*A61N 5/10* (2006.01)

(52) U.S. Cl.
CPC ........... *A61K 51/1282* (2013.01); *A61B 17/068* (2013.01); *A61B 17/07207* (2013.01); *A61B 2017/07214* (2013.01); *A61B 2017/07271* (2013.01); *A61B 2017/00473* (2013.01); *A61B 2017/00809* (2013.01); *A61B 2017/2923* (2013.01); *A61N 2005/1011* (2013.01)
USPC ....... 227/176.1; 227/175.1; 227/19; 606/139; 606/219

(58) Field of Classification Search
USPC ............... 227/175.1, 176.1, 19; 606/139, 219
See application file for complete search history.

(56) References Cited

U.S. PATENT DOCUMENTS

| 6,945,141 | B2 | 9/2005 | Hu |
| 7,494,039 | B2 | 2/2009 | Racenet et al. |
| 7,510,107 | B2 | 3/2009 | Timm et al. |
| 7,604,151 | B2 | 10/2009 | Hess et al. |
| 7,604,586 | B2 | 10/2009 | Wazer et al. |

OTHER PUBLICATIONS

Jemal, Siegel, et al. "Cancer Statistics, 2009." CA Cancer J Clin. 2009;59:225-249.
American College of Surgeons. "National Cancer Database for 2003." <http://www.facs.org/cancer/ncdb/index.html>.
Ginsberg, R. J. and L.V. Rubinstein. "Randomized Trial of Lobectomy Versus Limited Resection for T1 N0 Non-Small Cell Lung Cancer." Lung Cancer Study Group Ann Thorac Surg. Sep. 1995;60(3):615-22. <http://ats.ctsnetjournals.org/cgi/content/full/60/3/615>.
Martini, Bains, et al. "Incidence of Local Recurrence and Second Primary Tumors in Resected Stage I Lung Cancer." J Thorac Cardiovasc Surg. Jan. 1995;109(1):120-9.

(Continued)

*Primary Examiner* — Michelle Lopez
(74) *Attorney, Agent, or Firm* — Stan Collier, Esq.

(57) ABSTRACT

A staple delivery applicator for delivering radioactive staples during brachytherapy medical treatment has an actuating device for attaching source staples located distally thereform. The actuating device is removably attachable to an actuator arm on a proximal end. A staple applicator cartridge holder is attached to the actuator arm on a distal end. The staple applicator cartridge is mountable in the holder and has slots for mounting of radioactive source staples therein. An anvil therein crimps the staples. The staple applicator cartridge holder is removably mountable in a connector and the connector is also removably mounted to a surgical staple holder. A trigger device has a control for closing the anvil of the cartridge holder and for firing of the source staples in the cartridge therein to cause the staples to crimp, and a control for opening the anvil and releasing the trigger device from the actuator arm.

6 Claims, 19 Drawing Sheets

(56) References Cited

OTHER PUBLICATIONS

Ichinose, Yano, et al. "The Correlation Between Tumor Size and Lymphatic Vessel Invasion in Resected Peripheral Stage I Non-Small-Cell Lung Cancer." A potential risk of limited resection. J Thorac Cardiovasc Surg. Oct. 1994;108 (4):684-6.

Choi, N. C. "Prospective Prediction of Postradiotherapy Pulmonary Function With Regional Pulmonary Function Data: Promise and Pitfalls." Int J Radiat Oncol Biol Phys. Jul. 1988;15(1):245-7.

Landreneau, Sugarbaker, et al. "Wedge Resection Versus Lobectomy for Stage I (T1 N0 M0) Non-Small-Cell Lung Cancer." J Thorac Cardiovasc Surg. Apr. 1997;113(4):691-8; discussion 698-700.

Warren, W. H. and L.P. Faber. "Segmentectomy Versus Lobectomy in Patients With Stage I Pulmonary Carcinoma." Five-Year Survival and Patterns of Intrathoracic Recurrence. J Thorac Cardiovasc Surg. Apr. 1994;107 (4):1087-93.

Kodama, Doi, et al. "Intentional Limited Resection for Selected Patients With T1 N0 M0 Non-Small-Cell Lung Cancer: A Single-Institution Study." J Thorac Cardiovasc Surg. Sep. 1997;114(3):347-53.

Miller, J.I. and C. R. Hatcher, Jr. "Limited Resection of Bronchogenic Carcinoma in the Patient With Marked Impairment of Pulmonary Function." Ann Thorac Surg. Oct. 1987;44(4):340-3.

Hilaris, B. S. and D. Nori. "The Role of External Radiation and Brachytherapy in Unresectable Non-Small Cell Lung Cancer." Surg Clin North Am. Oct. 1987;67(5):1061-71.

Fleischman, Kagan, et al. "Iodine125 Interstitial Brachytherapy in the Treatment of Carcinoma of the Lung," J. Surg Oncol. Jan. 1992; 49(1):25-8.

National Cancer Institute. "Phase III Randomized Study of Sublobar Resection With Versus Without lntraoperative Brachytherapy in High-Risk Patients With Stage I Non-Small Cell Lung Cancer." Protocol ID NCT00107172, ACOSOG-Z4032 SRCI. <http://www.cancer.gov/clinicaltrials/ACOSOG-Z4032>.

Lee, Daly, et al. "Limited Resection for Non-Small Cell Lung Cancer: Observed Local Control With Implantation of 125I Brachytherapy Seeds." Ann Thorac Surg. Jan. 2003;75(1):237-42.

Chen, Galloway, et al. "Intraoperative 125I Brachytherapy for High-Risk Stage I Non-Small Cell Lung Carcinoma." Int J Radiat Oncol Biol Phys. Jul. 15, 1999;44(5)1057-63.

Pisch, Belsley, et al. "Placement of 125I Implants With the Da Vinci Robotic System After Video-Assisted Thoracoscopic Wedge Resection: A Feasibility Study." Int J Radiat Oncol Biol Phys. Nov. 1, 2004;60(3):928-32.

Wazer, Dipetrillo, et al. "A novel brachytherapy source and delivery system for use in conjunction with VATS wedge resection of early-stage lung cancer". OR 64. Oral Presentations / Brachytherapy 8 (2009) 105-180.

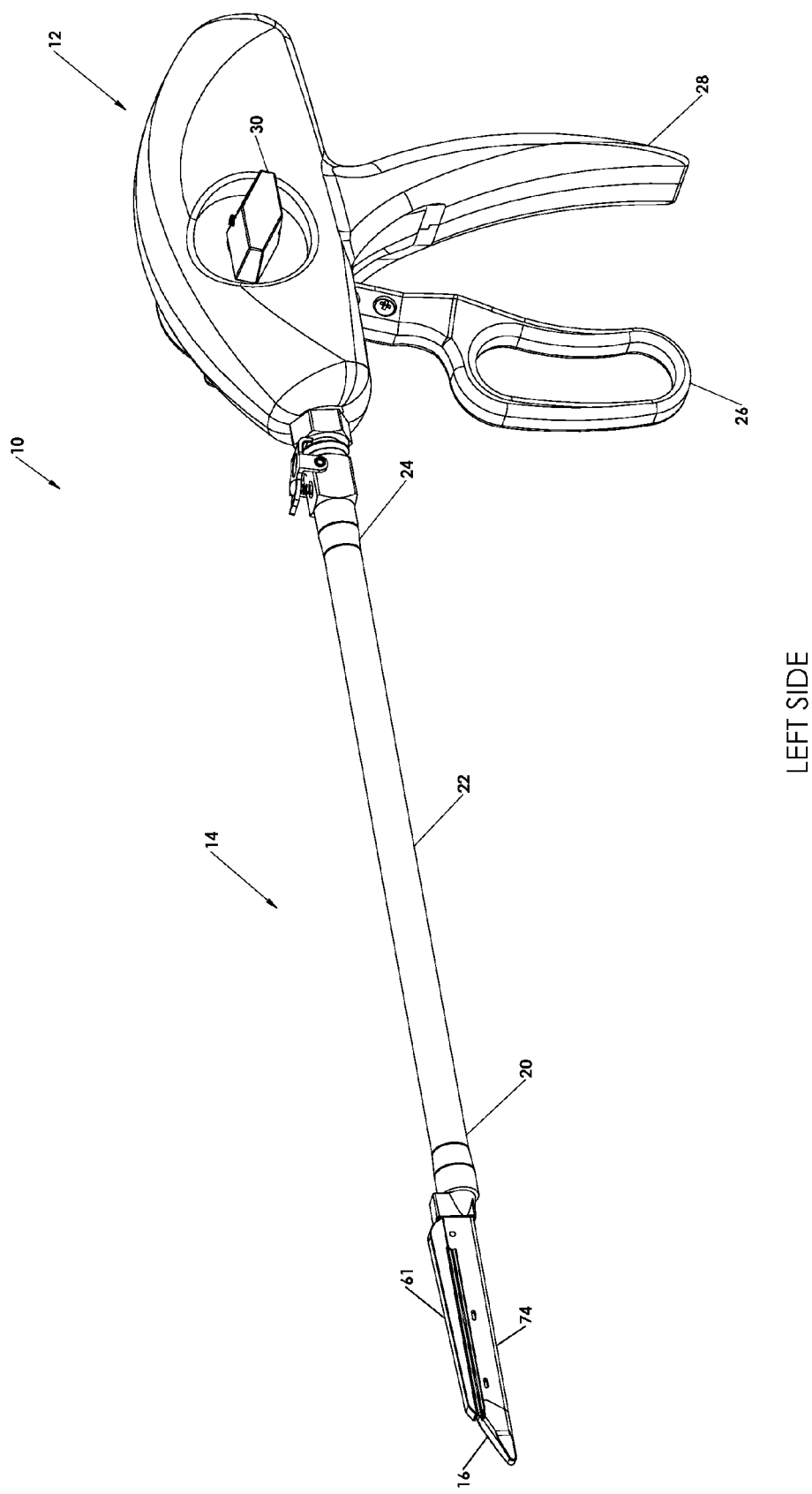

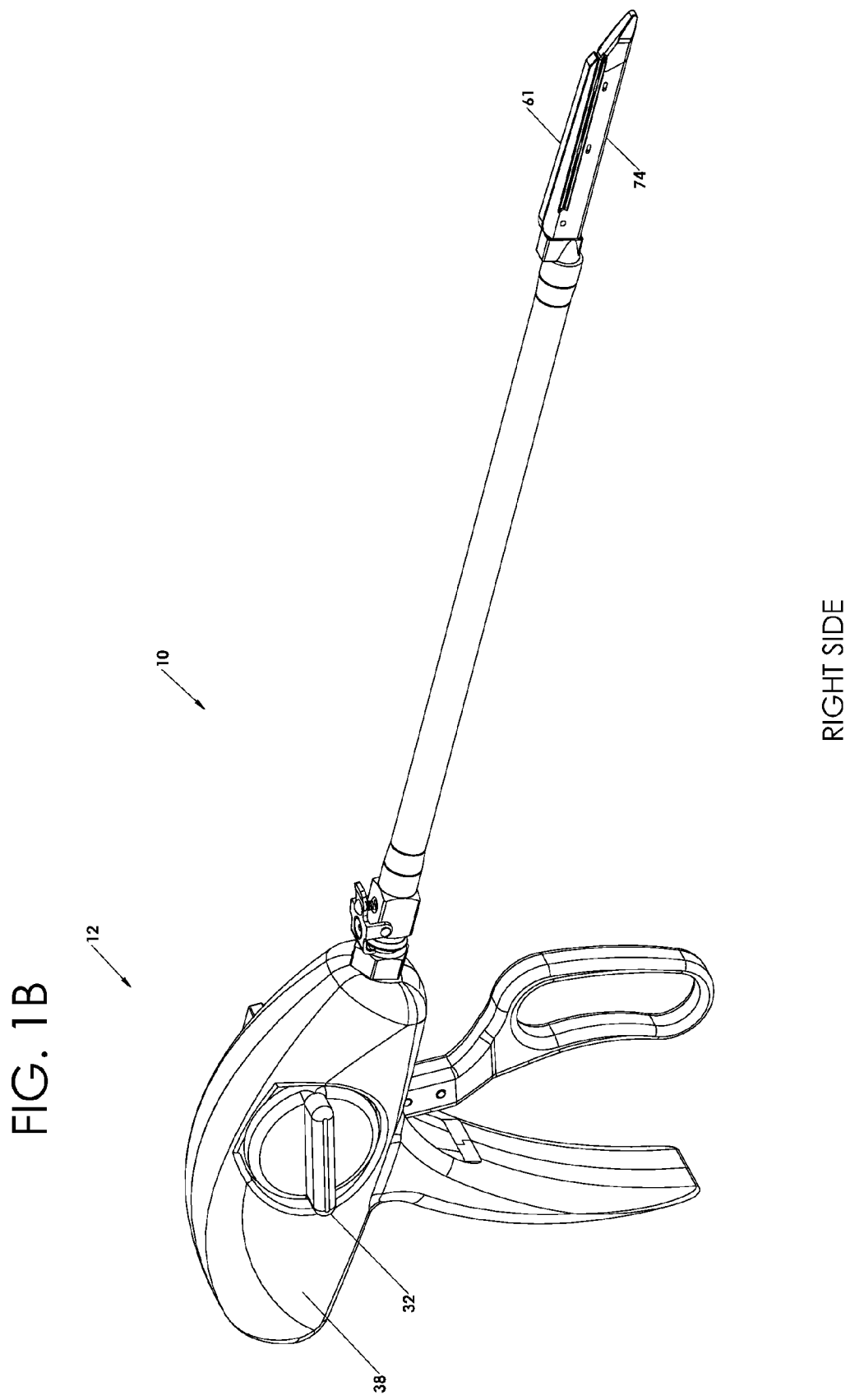

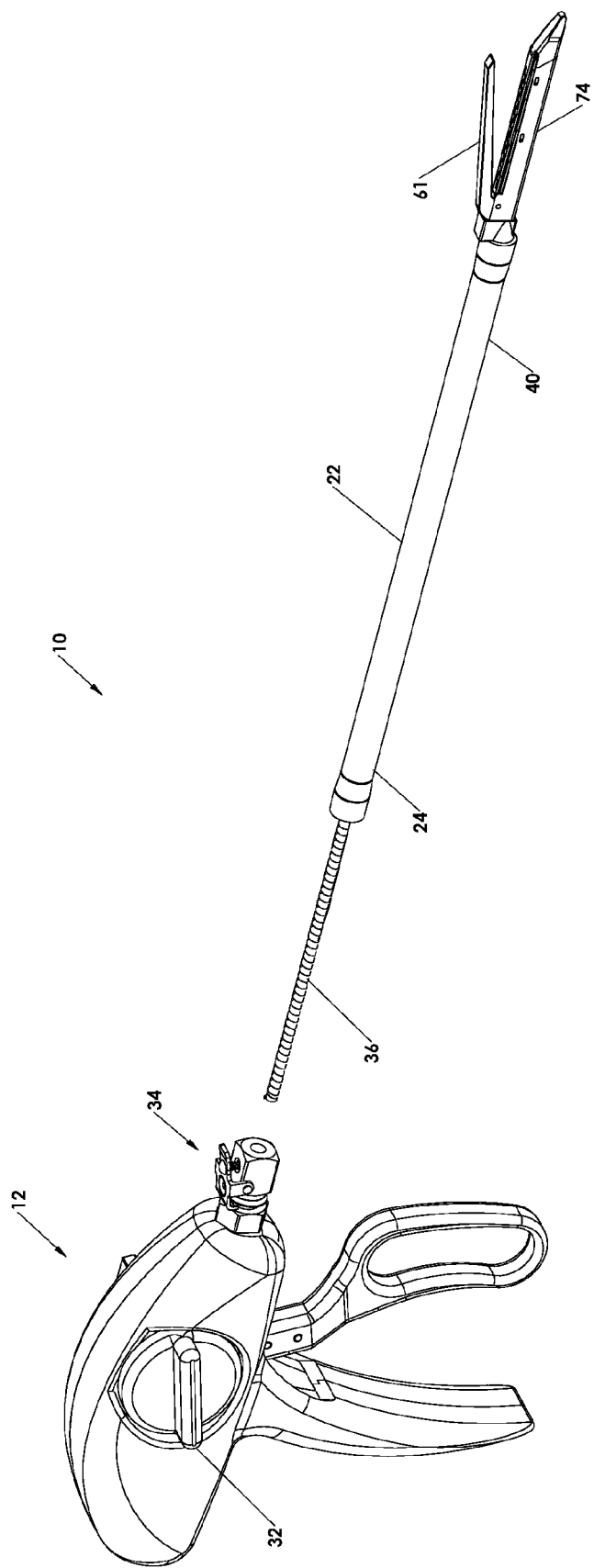

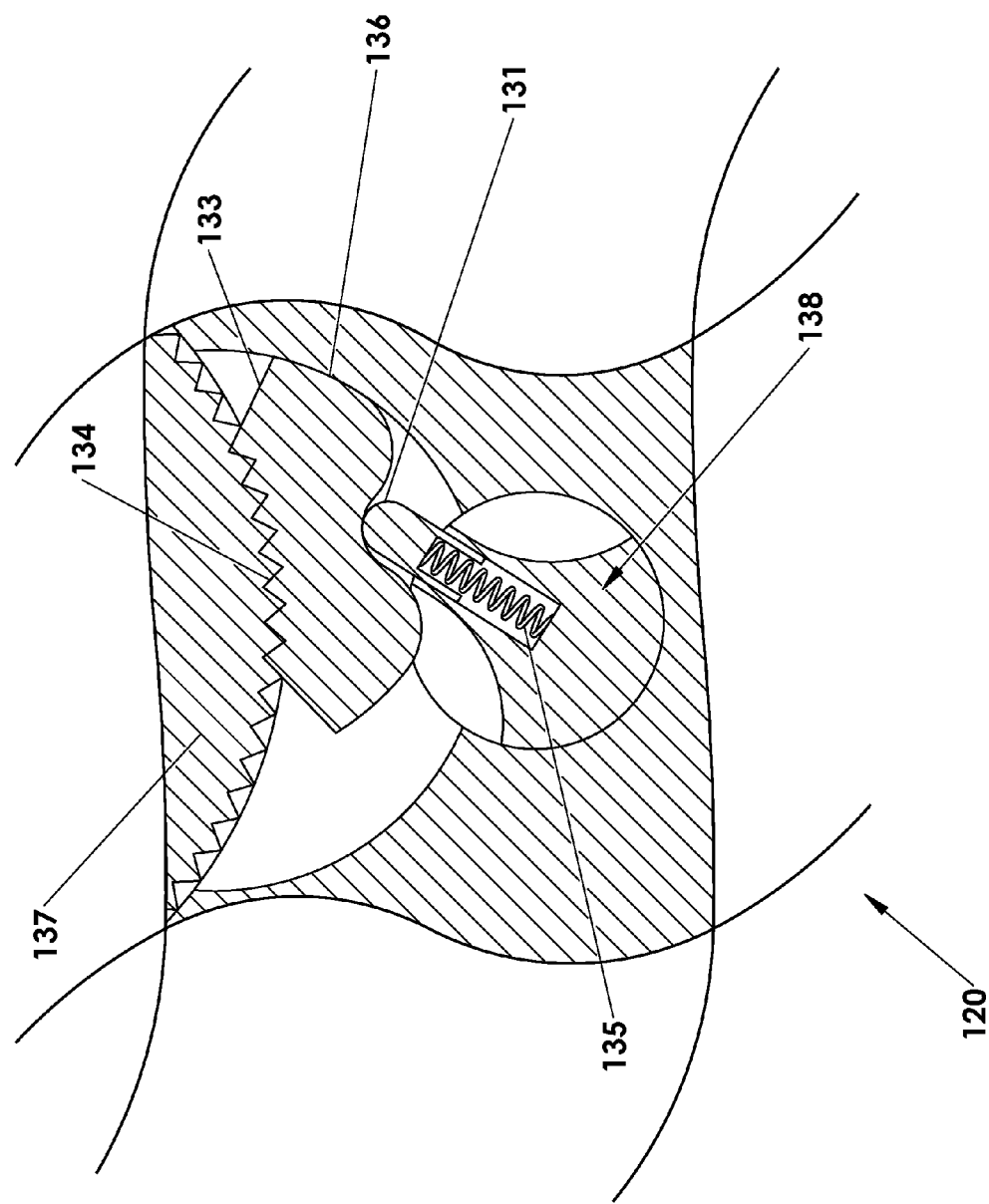

DELIVERY APPLICATOR FOR RADIOACTIVE STAPLES FOR BRACHYTHERAPY MEDICAL TREATMENT

REFERENCE TO FEDERALLY SPONSORED RESEARCH OR DEVELOPMENT

NIH Grant Numbers 1R43CA125999-01A1, 2R44CA125999-02, 5R44CA125999-03, and 3R44CA125999-03S1

CROSS REFERENCES TO RELATED APPLICATIONS

NA

REFERENCE TO JOINT RESEARCH AGREEMENTS

NA

REFERENCE TO SEQUENCE LISTING

NA

BACKGROUND OF THE INVENTION

1. Field of the Invention

The present invention relates generally to medical treatment, and, in particular, relates to the medical treatment by use of: brachytherapy, and, in greater particularity, relates to medical treatment by the use of multiple sources of radiation using a staple applicator.

2. Description of the Prior Art

The use of stapling devices for lung resection is necessary due to the complex nature of the lung and the treatment where there is poor pulmonary health or other medical issues that do not allow lobectomy.

When removing non-small cell lung cancers, the most prevalent form of lung cancer, for example, the use of radioactive sources near the cancer site provides another mode of treatment. One issued patent discloses the use of staples containing a radioactive material and the attachment of these staples near the surgical resection. These staples are placed in conventional staple cartridges and are thus placed near the resection.

The following references are incorporated by reference: U.S. Pat. Nos. 6,945,141; 7,494,039; 7,510,107; 7,604,151; and; 7,604,586.

Accordingly, there is an established need for a staple delivery applicator having means for accurate placement of the radioactive staples in surgical sites.

SUMMARY OF THE INVENTION

The present invention is directed at a staple delivery applicator for use with radioactive staples.

A staple delivery applicator for delivering radioactive staples during brachytherapy medical treatment has an actuating device for attaching source staples located distally from the actuating device. The actuating device is removably attachable to an actuator arm on a proximal end. A staple applicator cartridge holder is attached to the actuator arm on a distal end. The staple applicator cartridge is mountable in the holder and having a plurality of slots for mounting of radioactive source staples therein. An anvil therein crimps the staples. The staple applicator cartridge holder is removably mountable in a connector and the connector is also removably mounted to a surgical staple holder. In one embodiment a trigger device has a control for closing the anvil of the cartridge holder and for firing of the source staples in the cartridge therein to cause the staples to crimp, and a control for opening the anvil and releasing the trigger device from the actuator arm.

An object of the present invention is to provide a means for irradiating cancer tissue with the use or staples in lung, colorectal and gynecological cancers, for example.

It is another object of the present invention to provide an effective therapeutic modality for patients unable to undergo a surgical lobectomy; it is an alternative to external beam irradiation for patients who cannot tolerate further loss of lung function.

It is a further object of the present invention to provide a means to precisely deliver the brachytherapy sources intraoperatively to achieve the proper dose distribution and minimizing the radiation dose to the clinicians performing the procedure.

It is still a further object of the present invention to provide a means for precise placement of brachytherapy sources relative to the surgical margin, assuring the sources remain fixed in their precise positions for the duration of the treatment, overcoming the technical difficulties of manipulating the sources through the narrow surgical incision, and reducing the radiation dose to the clinicians.

It is yet a further object of the present invention to provide a delivery device having better shielding than the existing stapler cartridges, thereby providing greater safety to the physician and other operating room personnel.

It is yet a further object of the present invention, to provide a device that reduces the possibility of mis-locating sources by reducing and/or by limiting the number of: potential source positions to only dosimetrically useful positions, rather than all staple positions, and further locating the sources nearer to the center of the treatment volume rather than at its edge.

These and other objects, features, and advantages of the present invention will become more readily apparent from the attached drawings and the detailed description, of the preferred embodiments, which follow.

BRIEF DESCRIPTION OF THE DRAWINGS

The preferred embodiments of the invention will hereinafter be described in conjunction with the appended drawings provided to illustrate and not to limit the invention, where like designations denote like elements, and in which:

FIG. 1A is a left side perspective view of an applicator of the present invention;

FIG. 1B is right side perspective view of the applicator of FIG. A of the present invention;

FIG. 2 is a right side view of a cartridge unit separated from a trigger of FIG. 1A of the present invention;

FIGS. 3C to 3D show a reverse switch. mechanism that interacts with the toggle rods of the toggle knob for changing the direction of cable movement; this being one possible mechanism;

Like reference numerals refer to like parts throughout the several views of the drawings.

DETAILED DESCRIPTION OF THE PREFERRED EMBODIMENTS

Figure 1C:
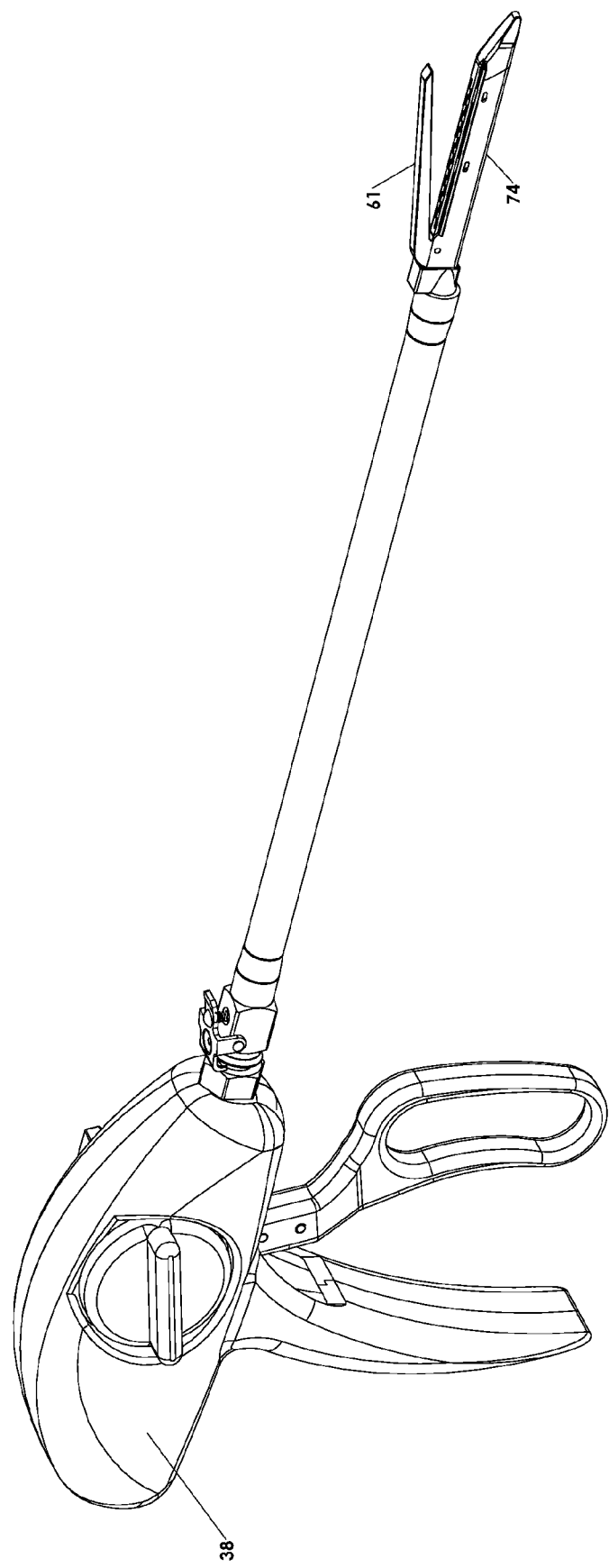
FIG. 1C is a right side perspective view of the applicator of FIG. 1B showing an anvil of a cartridge in the open position of the present invention.

The present invention is directed at a radioactive staple delivery applicator applicable to surgical procedures having the need for attaching radioactive devices.

The incidence of lung cancer has been rising over the last half century, although the rate has decreased somewhat over the last decade because of increased publicity about the health risks. The American Cancer estimates the number of new cases in 2009 to exceed 219,000. Lung cancer is the leading cause of cancer deaths in the United States among both men and women, expected to reach 159,000 in 2009, claiming more lives than colon, prostate and breast cancer combined.[i] (See IDS for references)

Non-small cell lung cancer (NSCLC) is the most commonly diagnosed form of the disease, affecting 4 out or 5 patients. In United States, ~23% of patients present with early-stage (T1, T2) disease.[ii] In most cases, early stage NSCLC can be treated successfully with surgery if the cancer has not spread beyond the chest. Surgical resection is the definitive treatment and lobectomy is the procedure of choice.[iii,iv,v] Lobectomy is the most common type of lung cancer surgery, involving removal of an entire lobe of one lung. For these early stage NSCLC patients, lobectomy yields a 5-year survival rate of 65-77%. Locoregional recurrence occurs in 28% of T1N0 tumors submitted to thoracotomy, with the highest initial failure rates detected in the ipsilateral hemithorax.[vi, iii]

Unfortunately, some patients with this disease are poor candidates for lobectomy due to poor pulmonary health or other medical issues.

Stage I NSCLC patients with compromised. cardiopulmonary status may undergo limited surgical resections in an attempt at lung preservation while achieving adequate resection margins.[vii] However, lesser resections have been associated with an increased risk of local recurrence, even for small peripheral tumors.[viii] Nonetheless, limited resection is viewed as an acceptable alternative for patients with poor physiologic reserve or of advanced age.[vii, ix]

Though sublobar resection alone is associated with an increased incidence of post-operative disease recurrence, it is still advocated for high-risk patients in the absence of a good alternative. External beam radiation therapy has been used successfully to reduce the risk of local recurrence in these compromised patients.[x] However, external beam radiation therapy further reduces pulmonary function because it generally requires the beam to pass through normal lung tissue to reach the target lesion. Some studies suggest that adding brachytherapy to the regimen can make a dramatic difference in outcomes.

Intraoperative brachytherapy has been shown to be an effective therapeutic modality for patients unable to undergo a surgical lobectomy; it is an alternative to external beam irradiation for patients who cannot tolerate further loss of lung function.[xi, xii]

The use of brachytherapy has been shown in several studies to have a clinical benefit for compromised lung cancer patients for whom more traditional surgical procedures, such as a lobectomy, are not an option. This is now the subject of a NTH-sponsored Phase III Clinical trial.[xiii]

Use of Brachytherapy: These candidate patients would. undergo limited (sublobar) surgical resection. (wedge resection) in an attempt at lung preservation while achieving adequate resection margins, followed by brachytherapy. Currently, brachytherapy is performed using $^{125}$Iodine seeds delivered at the time of surgery. Seeds have been deployed by a variety of techniques such as manually suturing stranded seeds,[xiv] manually delivering loose seeds via a Mick® applicator, thoracoscopic placement of vicryl mesh imbedded with $^{125}$Iodine radioactive seeds, and seed placement in the wedge resection margin using the da Vinci robotic system.[xvi]

The problem with all of these techniques is the difficulty in precisely delivering the brachytherapy seeds intraoperatively to achieve the proper dose distribution and minimizing the radiation dose to the clinicians performing the procedure.

The present invention will facilitate the precise placement of brachytherapy sources relative to the surgical margin, assure the sources remain fixed in their precise positions for the duration of the treatment, overcome the technical difficulties of manipulating the sources through the narrow surgical incision, and reduce the radiation dose to the clinicians.

The Source: The present invention provides "staple-like" sources that will be secured in position directly adjacent to the surgical resection and will be immobile. They will be precisely located relative to the resection, placed by a very convenient method eliminating the difficulties of working through the narrow surgical incision. The source position will be rigidly fixed, assuring the dose distribution will not uncontrollably change over the duration of the treatment. This method will permit the dose distribution to be precisely planned prior to the surgery to achieve the desired result. This technique will, also significantly reduce the dose to the clinician.

Turning to the drawings, wherein like components are designated by like reference numerals throughout the various figures, attention is initially directed to FIG. 1A, which illustrates by a perspective view a staple delivery applicator 10 constructed according to the present invention.

The staple delivery applicator 10 is composed of a trigger device 12 and a cartridge unit 14, FIG. 1A, with a source staple cartridge 16 mounted in a cartridge holder 74. The cartridge holder 74 is mounted to a distal end 20 of an actuator arm 22 by a cartridge holder 74/actuator arm connector 107, FIG. 5A. The cable 36/sled connector 118, FIGS. 5A and 5B, allows flexible movement between the cable 36 and the sled 102 within the actuator arm 22. The actuator arm 22 is removably mounted to the trigger device 12 at a proximal end 24 by a release lever 34. The trigger device 12 has multiple controls thereon to operate the attachment of the staples, not shown.

The trigger device 12 has a lever 26, a handle 28, and a release knob 30 as shown in FIG. 1A, and a toggle knob 32, FIG. 1B.

FIG. 1B shows the right side of the applicator 10 and the trigger 12 having the toggle knob 32 thereon. FIG. 1C shows the applicator 10 having an. anvil 61 in the open position. FIG. 2 shows the actuator arm 22 removed from the trigger 12 with a cable 36 extending from a tube 40 at the proximal end 24. The spring loaded, release lever 34 allows the actuator arm 22 to be removed from the trigger 12 as needed.

Figure 3A:
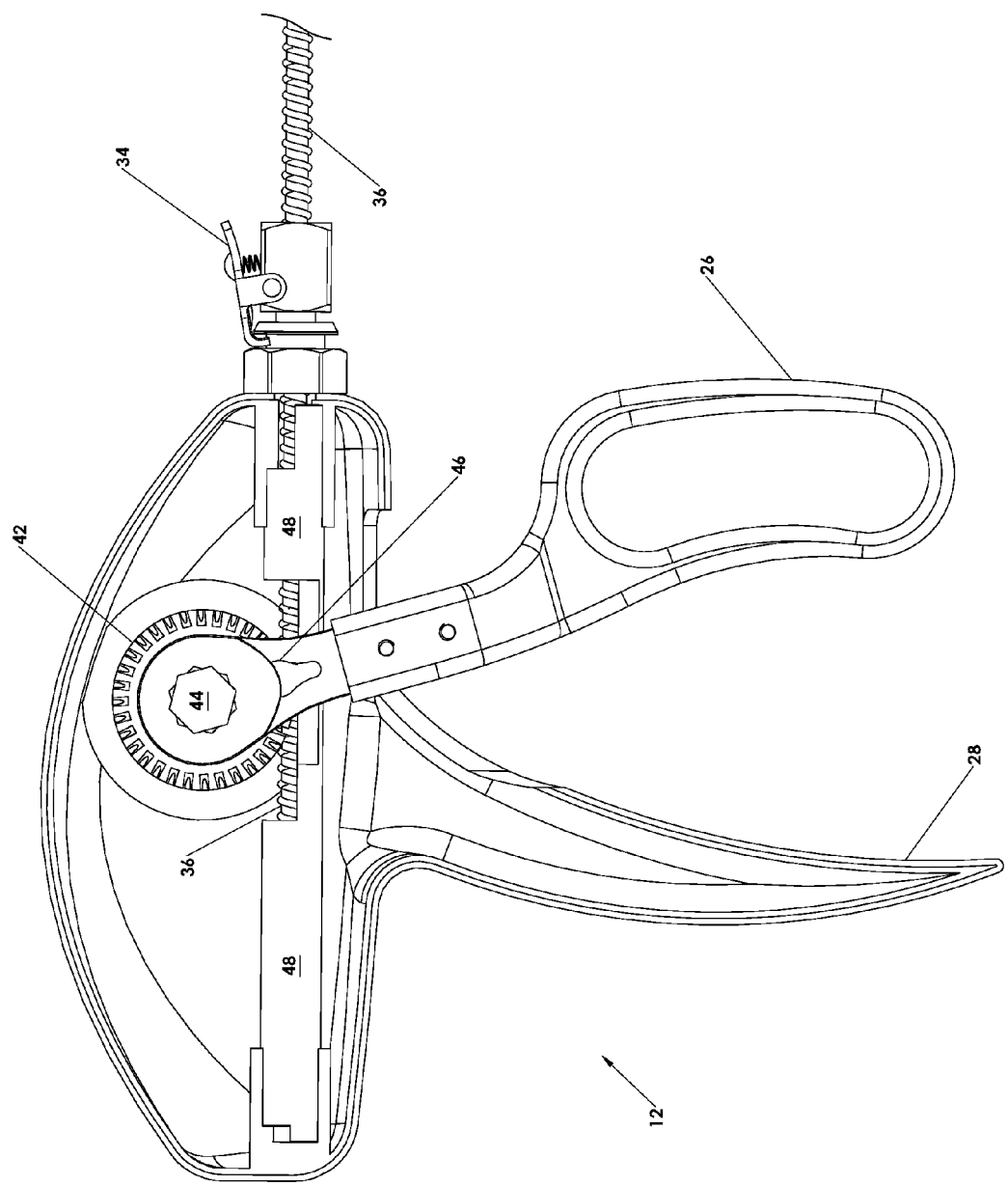
FIG. 3A is a right side view of the applicator of FIG. 1A having a right side housing removed. from the trigger of the present invention.
Figure 3B:
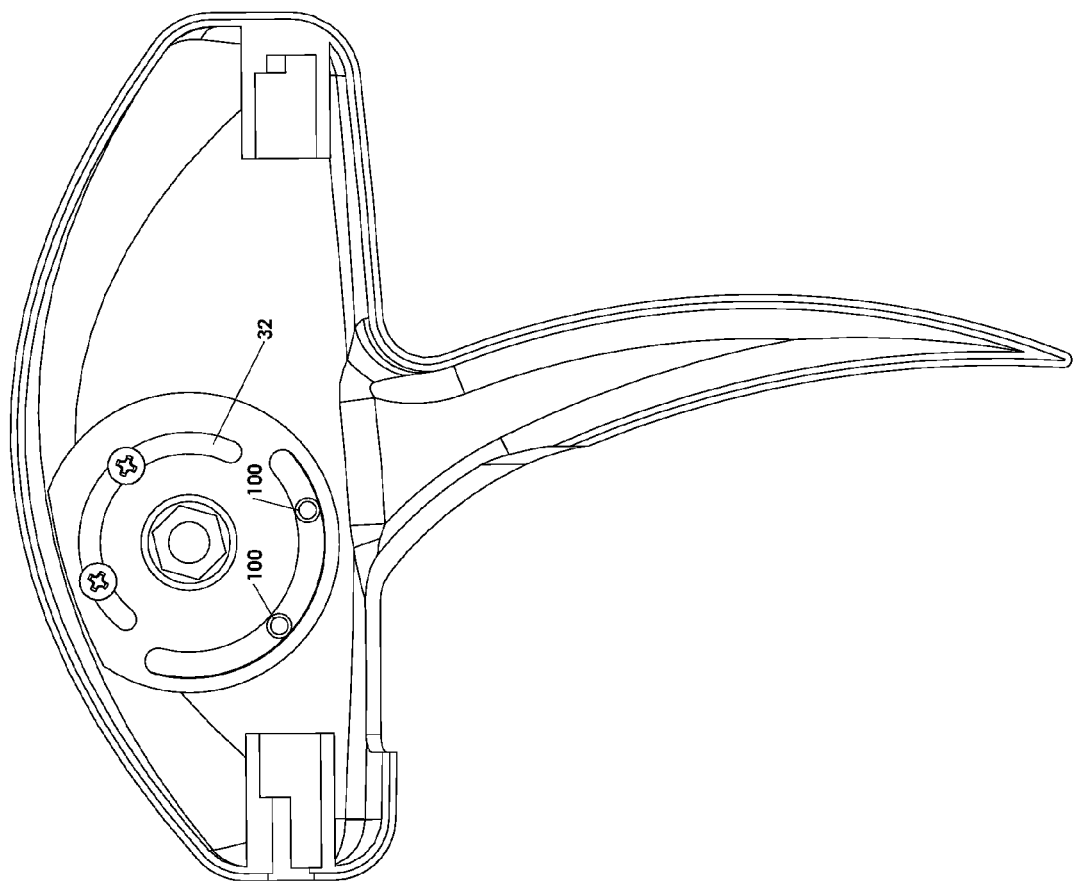
FIG. 3B is a left side view of the applicator having a left side housing removed from the trigger of the present invention, showing the back of the toggle knob on the right side of the applicator of FIG. 1B.
Figure 3C:
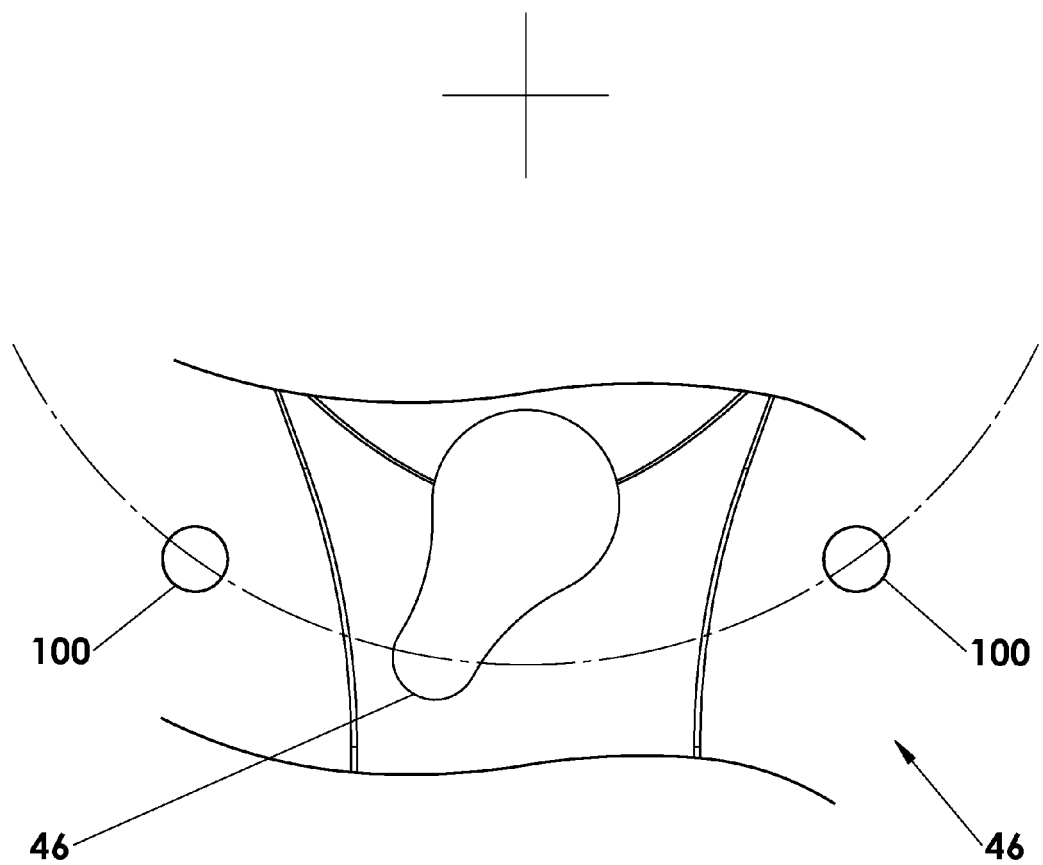

Referring to FIG. 3A, a right side housing 38 is removed from the trigger 12 to show partially the interior thereof. A gear 42 is mounted to a central shaft 44. The gear 42 translates/acts upon the cable 36 that is supported within cable guides 48. The back of the toggle knob 32, FIG. 3B, has a pair of toggle rods 100 that act upon a toggle switch 46, FIG. 3A. When the toggle switch 46 is reversed by the turning of the toggle knob. 32, the release knob 30 can be then turned to translate the cable 36 out of the trigger 12 to be released. FIG. 3D shows one embodiment of a reverse switch mechanism 120. The reverse switch mechanism 120 allows the gear 42 to reverse direction such as in a wrench ratchet As shown in FIG. 3D, a reverse switch mechanism 120 is comprised of a ratchet 137, which is connected to the central shaft 44, and a pawl 133. A spring 135 biases a lever 131 to hold the pawl 133 in place. The rotating member 138 is connected to the toggle switch 46, FIG. 3C. The pair of toggle rods 100 are shown in FIG. 3C with a travel line in dashes as the toggle knob 32 is turned. In operation, if the right toggle rod 100 is turned. clockwise, it will push the bottom of the toggle switch 46 clockwise to the position as shown in FIG. 3C. As a result, turning of the central shaft 44 in a counterclockwise direction is prohibited since the teeth of the ratchet and pawl are engaged 134 and the pawl hits a wall 136, preventing movement. Clockwise rotation is possible as this motion moves the ratchet 137 clockwise, pushing the pawl 133 into the lever 132 and compressing the spring 135. When the right toggle rod 100 is rotated counterclockwise, it pushes the bottom of the toggle switch 46 clockwise and the detent mechanism functions in the opposite direction. Clearly other embodiments of such a reverse switch are possible in light of the present invention and in light of the incorporated patents.

Figure 8A:
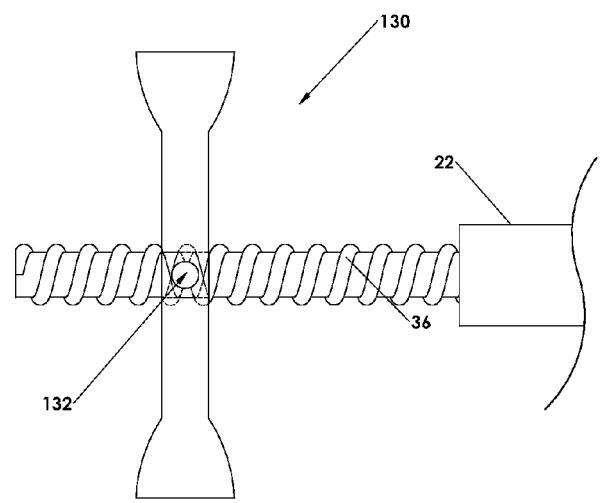
FIGS. 8A and 8B illustrate several actuating devices in addition to the trigger device as shown above for operating the cable attached to the cartridge unit.
Figure 8B:
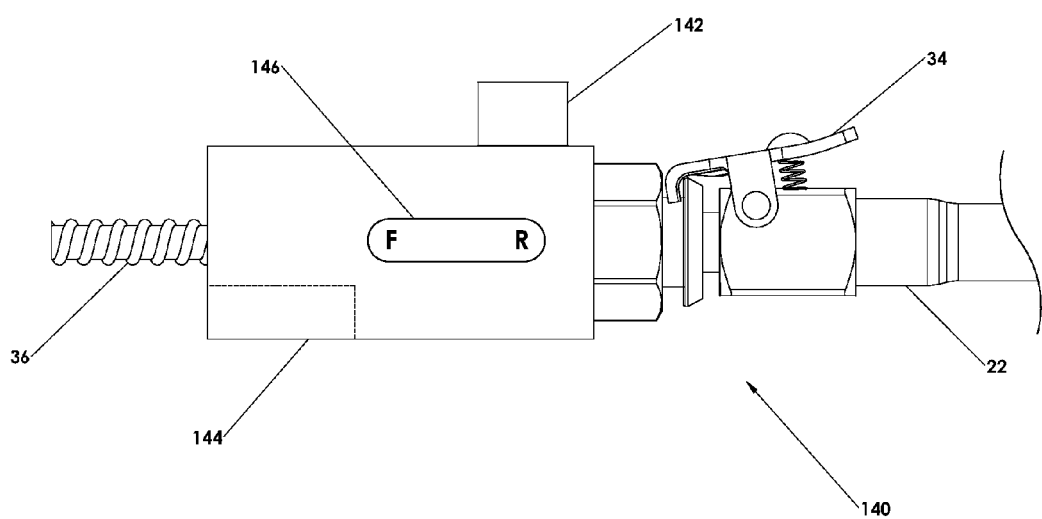

The trigger device 12 as shown above is one embodiment of an actuating means or device for operating the cable 36 in the actuating arm 22. Referring to FIGS. 8A and 8B, FIG. 8A illustrates a manual means for operating the cable 36 by attaching a handle 130 to the cable 36. It should be understood that the cable 36 has appropriate teeth thereon to engage the gear 42, but this is not required in that other actuating means may be used to move the cable 36. As shown, the handle 130 is attached to the cable 36 that extends from the actuating arm 22. The cable 36 is secured in the handle 130 by a locking means 132. The operator would then grasp the handle 130 and the tube 40 of the actuating arm 22 and move the cable 36 as desired and in a manner consistent with the movement noted above, Another embodiment of the actuating means is shown in FIG. 8B that is an electric actuating means 140 that is connected onto the actuating arm 22 by a release lever 34 such as shown on the trigger device 12. A power source 144 such as batteries or an external source provides power to a reversible electric motor 142 that is geared to mesh with the cable 36. A forward or reverse switch 146 is used to control the movement of the cable 36 within the actuating arm 22.

Figure 4A:
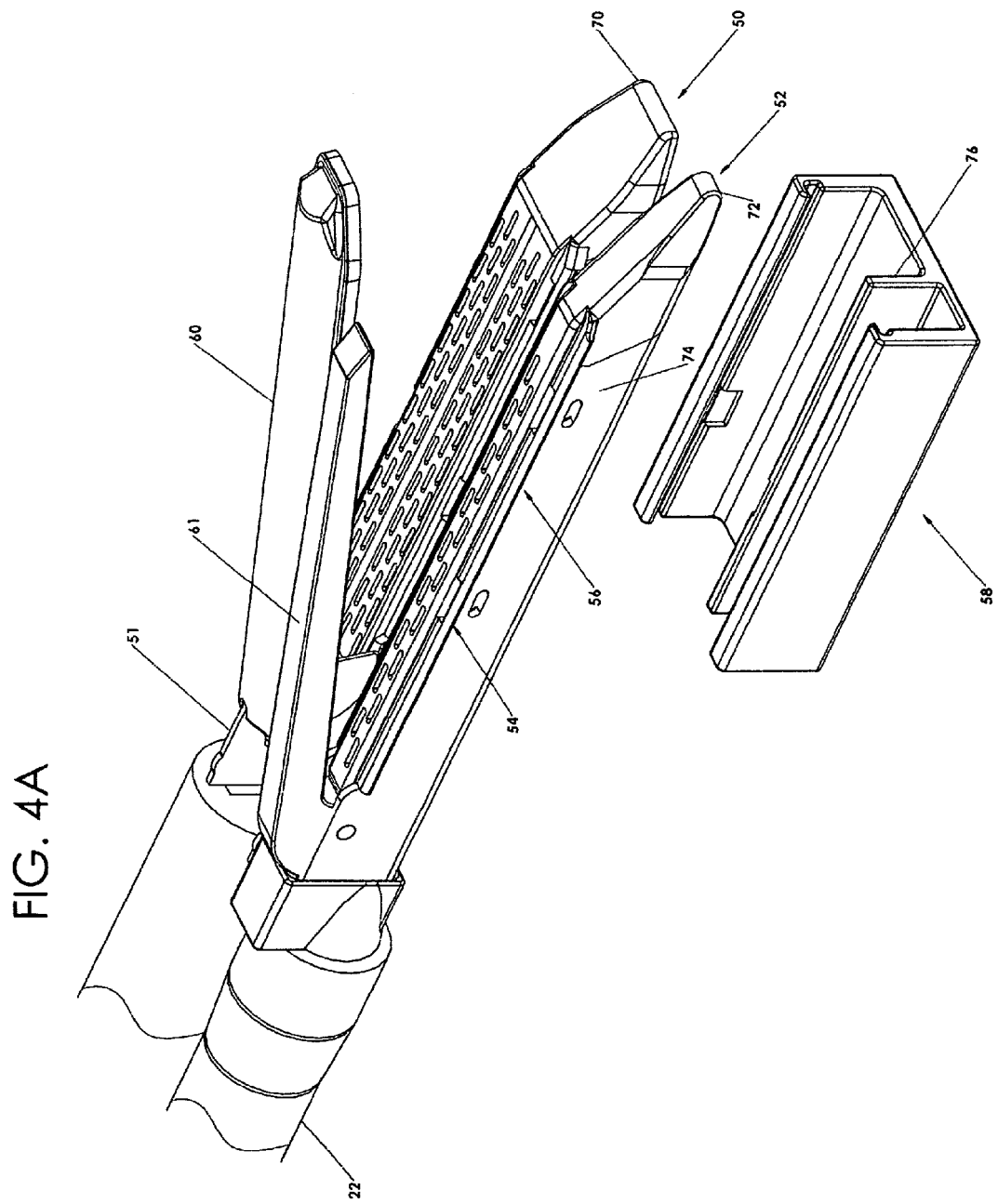
FIG. 4A is a partial perspective view of the cartridge unit of FIG. 2 along side of a surgical staple cartridge with a connector located below in the present invention.
Figure 5A:
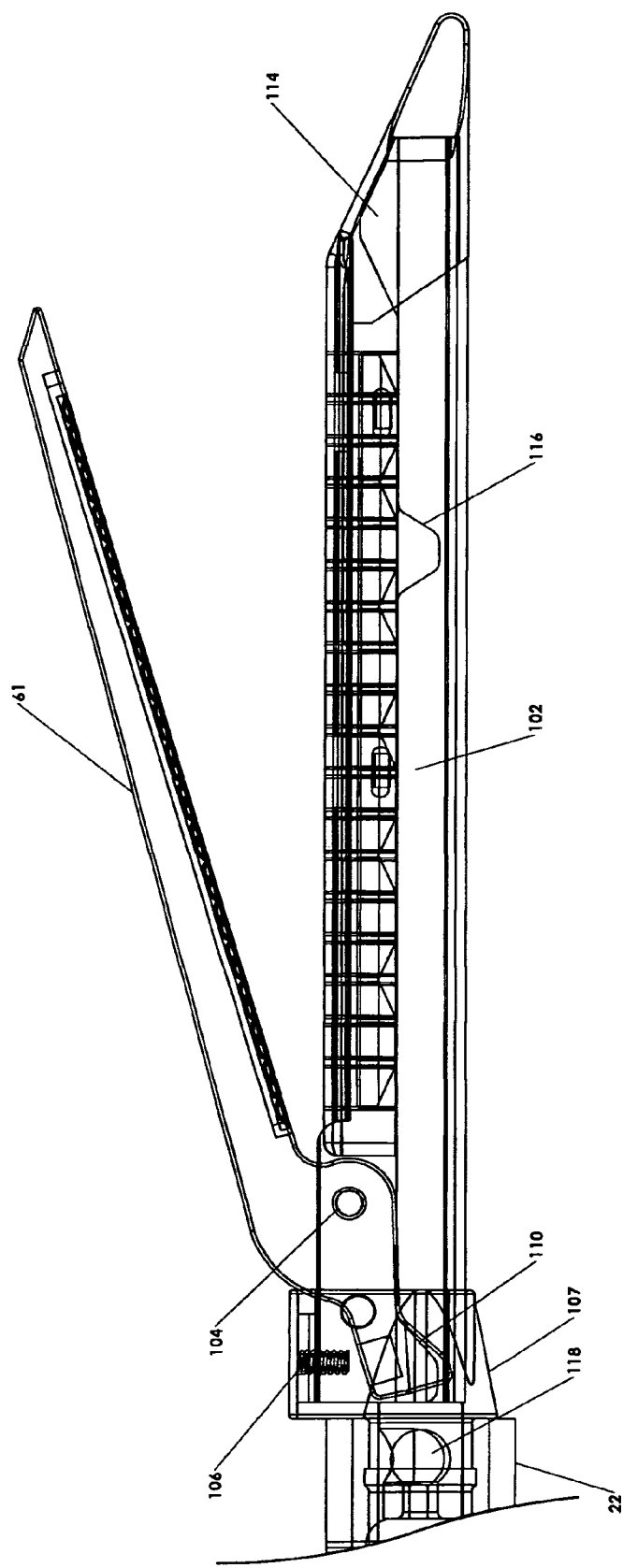
FIG. 5A is a partial side view of the cartridge unit of FIG. 2 with the anvil open showing by x-ray view an inside of the cartridge unit of the present invention.
Figure 5B:
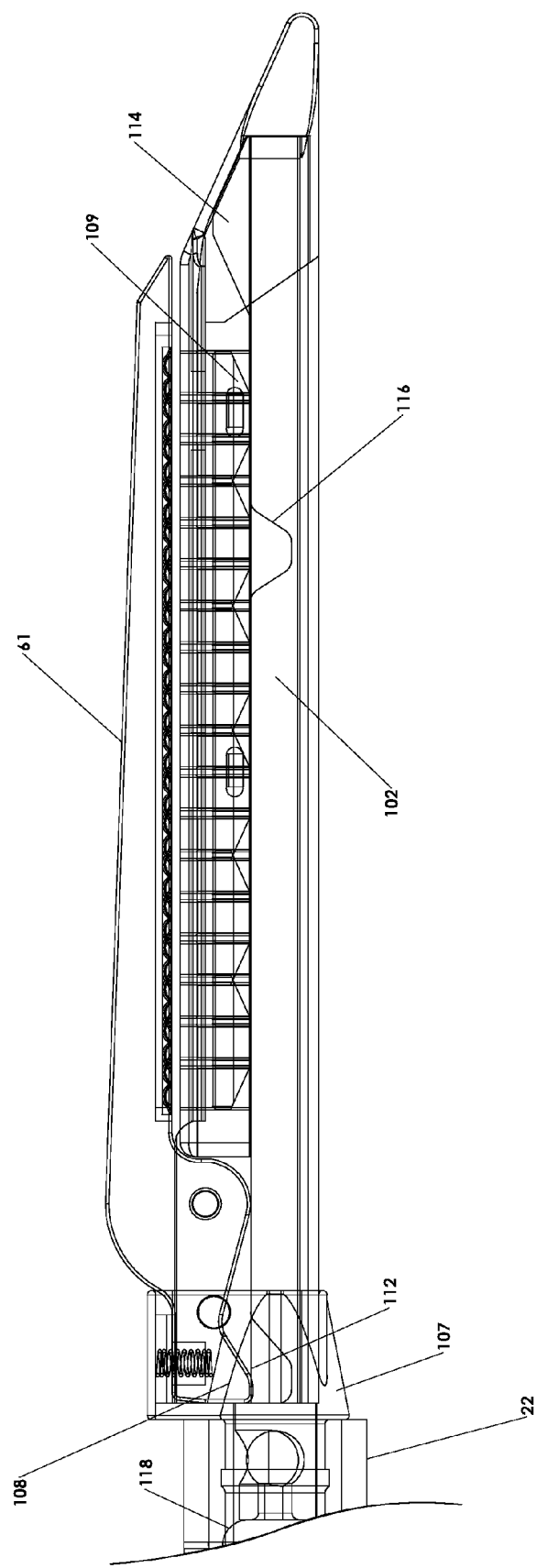
FIG. 5B shows the anvil closed as compared to FIG. 5A of the present invention.
Figure 6A:
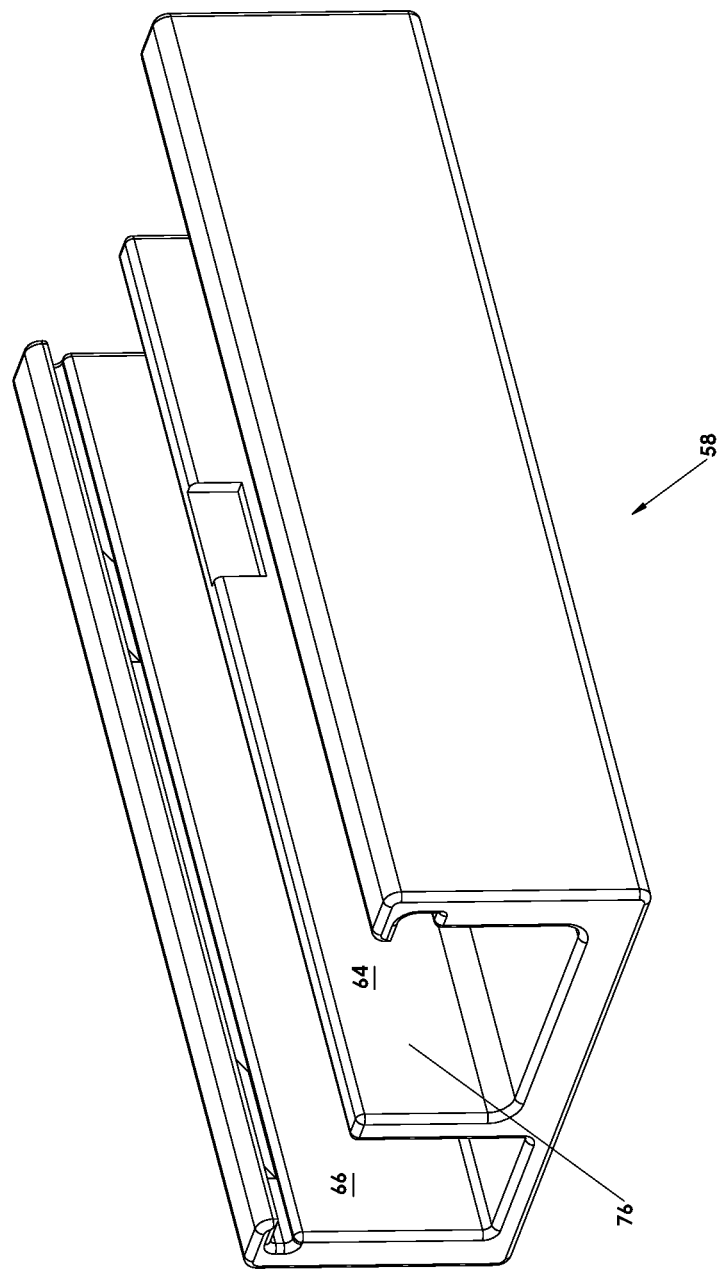
FIGS. 6A to 6D shows by perspective views one embodiment of the connector of the present invention.
Figure 6B:
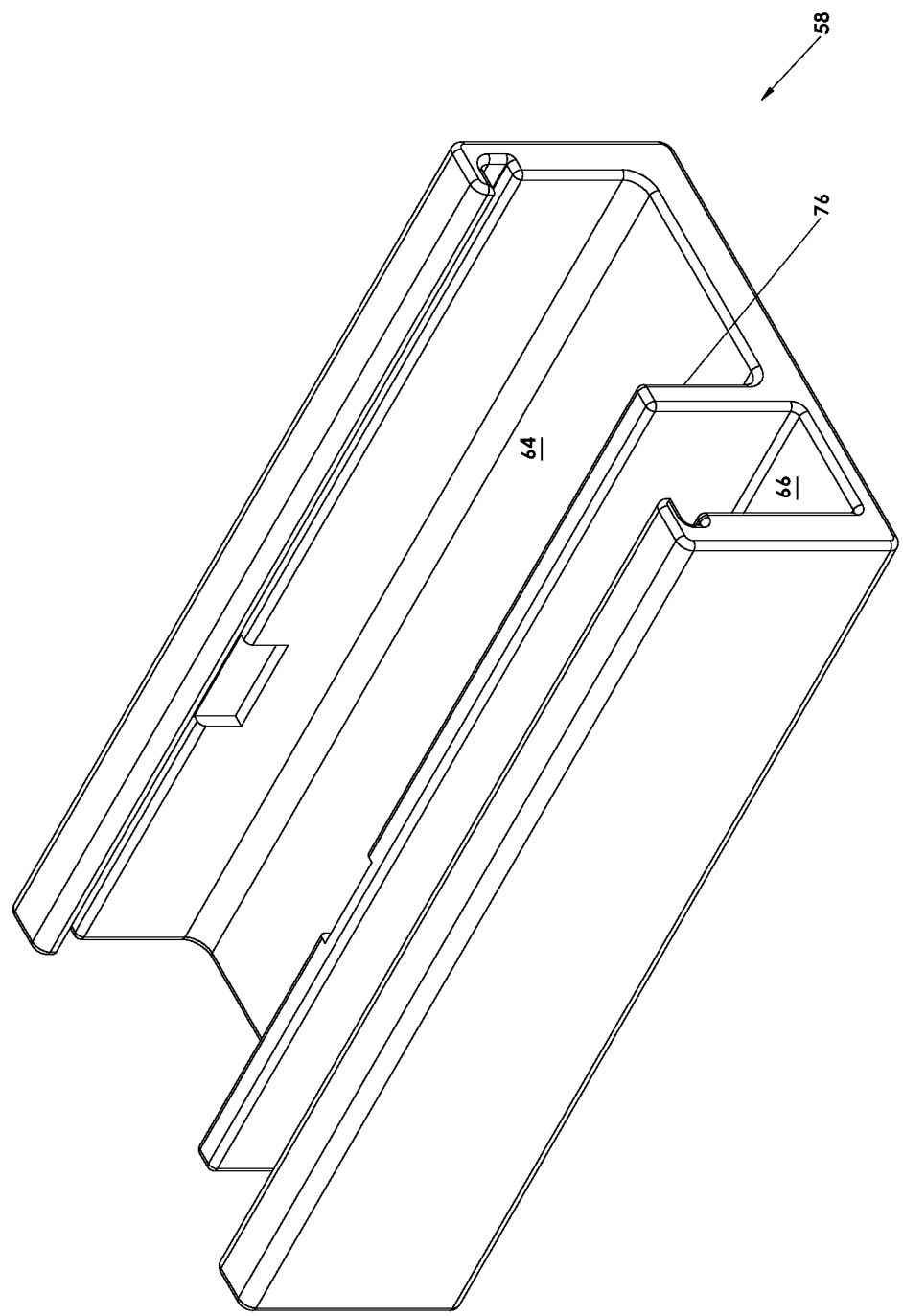
Figure 6C:
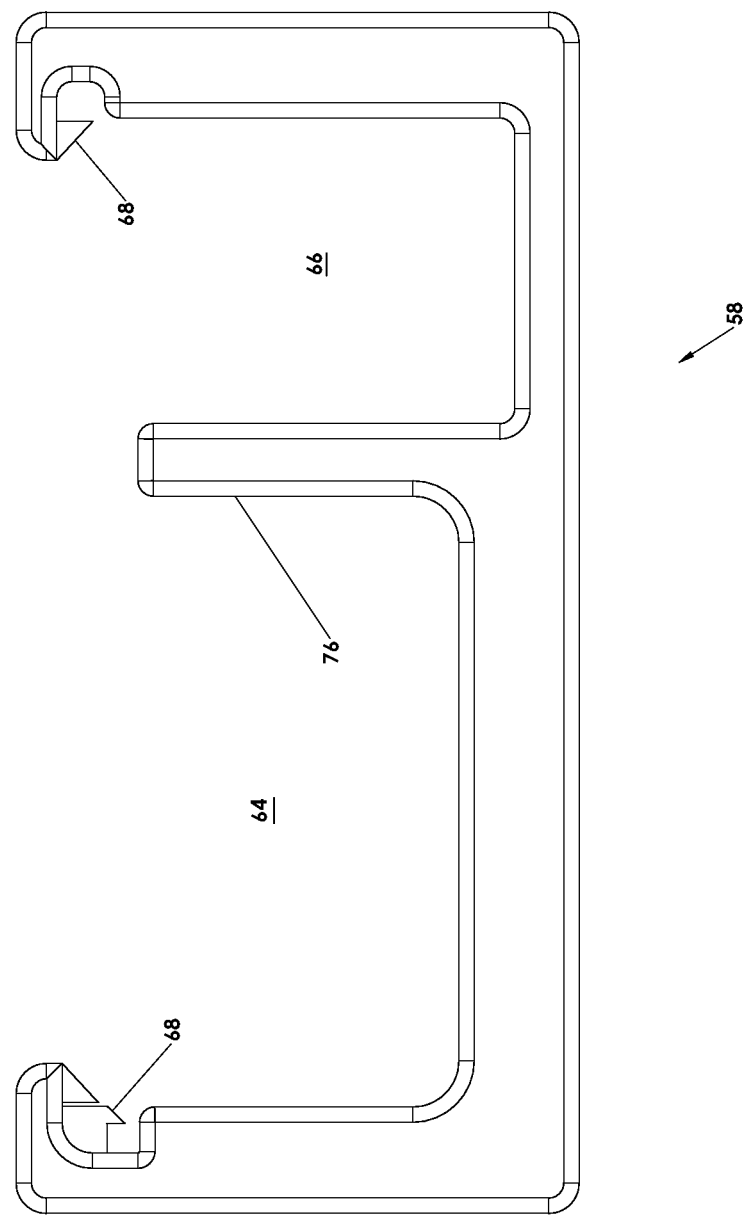
Figure 6D:
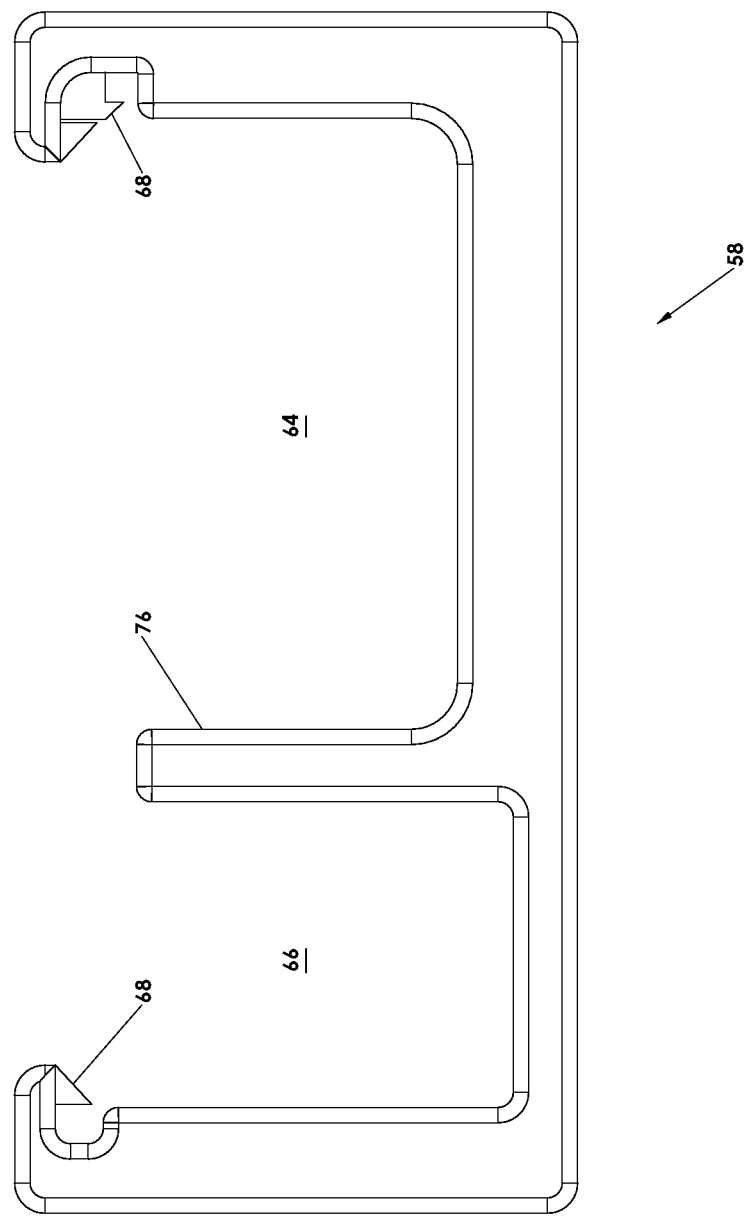

To better understand the operation of the applicator 10, FIGS. 1A, 3A, and 4A, the source cartridge 52 is loaded, into the source cartridge holder 74. With the cartridge 52 in place, the actuator sled 102, FIGS. 5A and 5B, is pushed toward the proximal end of the cartridge holder 74 and into the proximal end of the anvil 61 and causes the source anvil 61 to open as shown in FIG. 5A. The source anvil 61 is a part of the source staple cartridge holder 74 and is pivoted, at a pivot 104. An upper spring 106 forces an end 108 of the source anvil 61 into a first detent 110 to open. As the attached cable 36 is slightly retracted, the end 108 rides up an inclined, groove to a top 112 of the actuator sled 102 and closes the anvil 61, FIG. 5B. Further pulling of the lever 26 in a clockwise direction, to further retract the cable 36 causes a sled. hammer 114 to push up on the bottom of inclined pushers 109 that push up on the bottom of the source staples therein crimping them. After the crimping is completed, the end 108 fails into a second detent 116 in the sled 102 and then opens the anvil 61. The source cartridge 52 then can be removed. At that point, the cable 36 is fully retracted. In order to reverse the cable 36 movement in direction, at any time, the toggle knob 32 is rotated to cause the toggle rods 100, FIG. 3B, to change the position of the reverse switch 46. Then, toe release snob 30 is rotated to push the cable 36 back and the actuator sled. 102 back into the cartridge holder 74. The toggle knob 32 must then be reset to its initial setting so that the cable 36 can be retracted. Manual operation of the applicator 10 may be obtained by allowing the cable 36 to extend from a rear of the trigger 12 with the attachment of a handle thereon. The handle can be pulled to retract the cable 36 and pushed in to return the cable 36. The toggle knob 32 would have to be also appropriately turned in the manual operation.

Figure 4B:
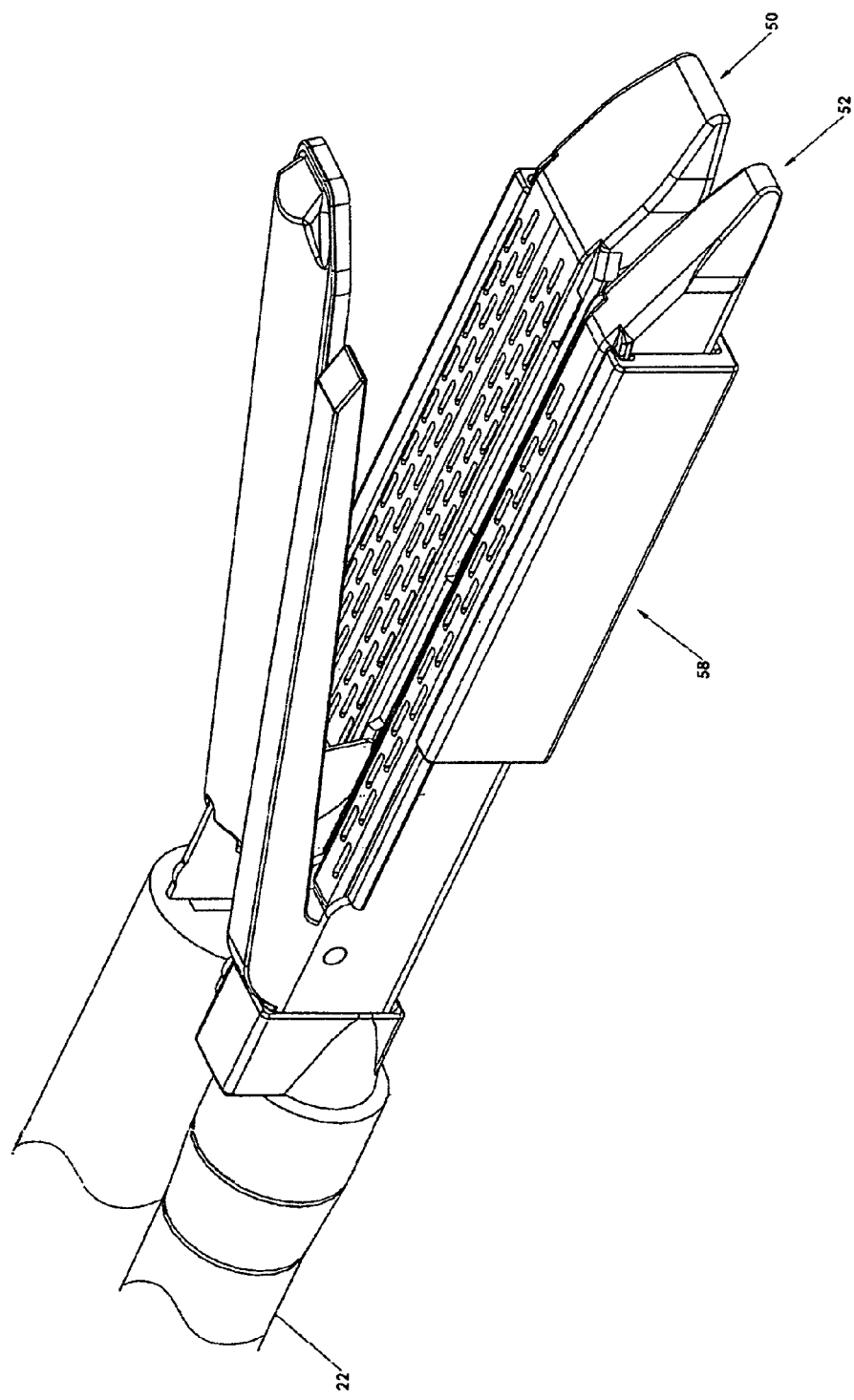
FIG. 4B is a partial perspective view as in FIG. 4A but showing the connector installed on the cartridges.

In one embodiment as best shown in FIGS. 4A and 4B, the delivery applicator 10 may be attached in a parallel manner to an existing surgical staple device 50 such as disclosed in U.S. Pat. No. 7,494,039. The applicator 10 may also be positioned in a parallel manner next to the surgical stapler cartridge as shown in FIG. 4B. The applicator cartridge 52 contains radioactive sources/staples, not shown (see U.S. Pat. No. 7,604, 586 showing radioactive staples which is incorporated by reference) in predetermined positions 54: two rows with staggered slots 56, FIG. 4A. Other configurations of the slots 56 are clearly appropriate and would be designed based upon the medical need for such. There may be a standard set of slots such as shown in FIG. 4A, but the source staples could be placed therein as desired. After deployment of the conventional surgical staples, not shown also, the applicator staples would be independently deployed by use of the trigger 12 immediately adjacent to the surgical staples. The fixed relationship by use of a connector 58 on the applicator cartridge 52 to the surgical staple cartridge 50 assures an accurate fixed position of the source/staples relative to the surgical staples, and therefore the surgical resection margin created by the surgical staple device having a cutting means therein.

Currently, surgical staples are delivered by a wedge-shaped driving element within the cartridge which presses a piston through the cartridge cavity causing the staples to be pressed against, an anvil 60 causing the staple legs to be bent over within an anvil bending device such as seen in a common stapler.

The applicator cartridge holder 74 is attached to either the right-hand or left-hand side of the surgical stapler cartridge 50 so as to be useful on either leg/side of a typical wedge resection. Source positioning will not be restricted to the typical. "1-centimeter" spacing that is currently used. The ability to have closer source positioning, especially at the ends of the line of sources, will afford the opportunity to differentially load the cartridge (i.e. have greater activity at the ends) to compensate for the dose "drop-off" typical of such an array of sources/seeds.

One embodiment of the present invention has a one-piece connector 58, FIGS. 6A to 6D and FIGS. 4A and 4B, for holding both the conventional surgical staple cartridge 50 and the applicator cartridge 52 in parallel alignment so that radioactive applicator staples can be applied directly along side of the conventional staples. This provides accurate placement of the radioactive applicator staples near possible cancerous tissues. The other embodiment of the connector is a modular connector 62, FIGS. 7A and 7B, for holding the applicator cartridge 52, which is connected to the conventional staple cartridge 50 also being held in the modular connector 62.

The staple delivery applicator 10 may use the connector 58, FIGS. 6A to 6D, being the one-piece connector 58 having two parallel channels 64 and 66 for holding the applicator cartridge 52 in channel 66 and the conventional staple cartridge 50 in the channel 64 such as shown in FIG. 4B. Sets of tabs 68, FIGS. 6C and 6D, in each channel align the cartridge holder 74 to detentes thereon wherein the front ends 70, 72, FIG. 4A, of each of the cartridges FIGS. 6A to 6D show the one-piece connector 58 in various views. This one-piece connector 58 may fit upon the carrier portion 250 as mentioned and shown in patent '039 above in FIG. 19. It should be noted that the surgical staple cartridge channel 64 is wider than the source/staple cartridge channel 66 since there are 6 slot rows in the surgical staple cartridge 50 as compared to 2 in the source cartridge 52. Further, the width of a separating wall 76 may be varied based on medical requirements. The connector is typically made of plastic and further may include radiation shielding material. The cartridges 50 and 52 are mounted in cartridge holders 74 and 51 that are then pushed. into the channels 64/66. The applicator holder 74 is connected to the actuator arm 22 as to the present invention.

Figure 7A:
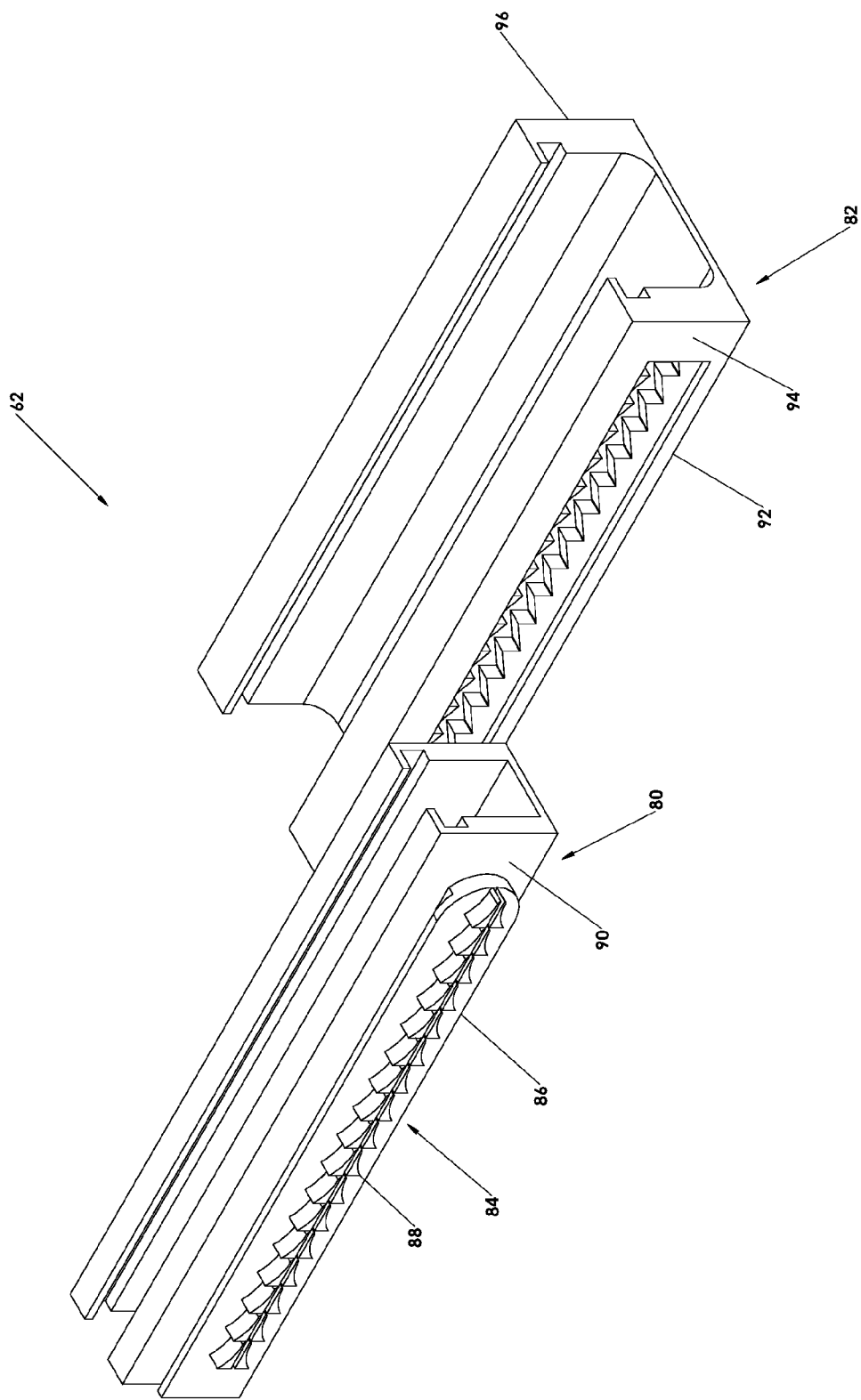
FIGS. 7A to 7B shows by perspective views the embodiment of both modular units being installed together.
Figure 7B:
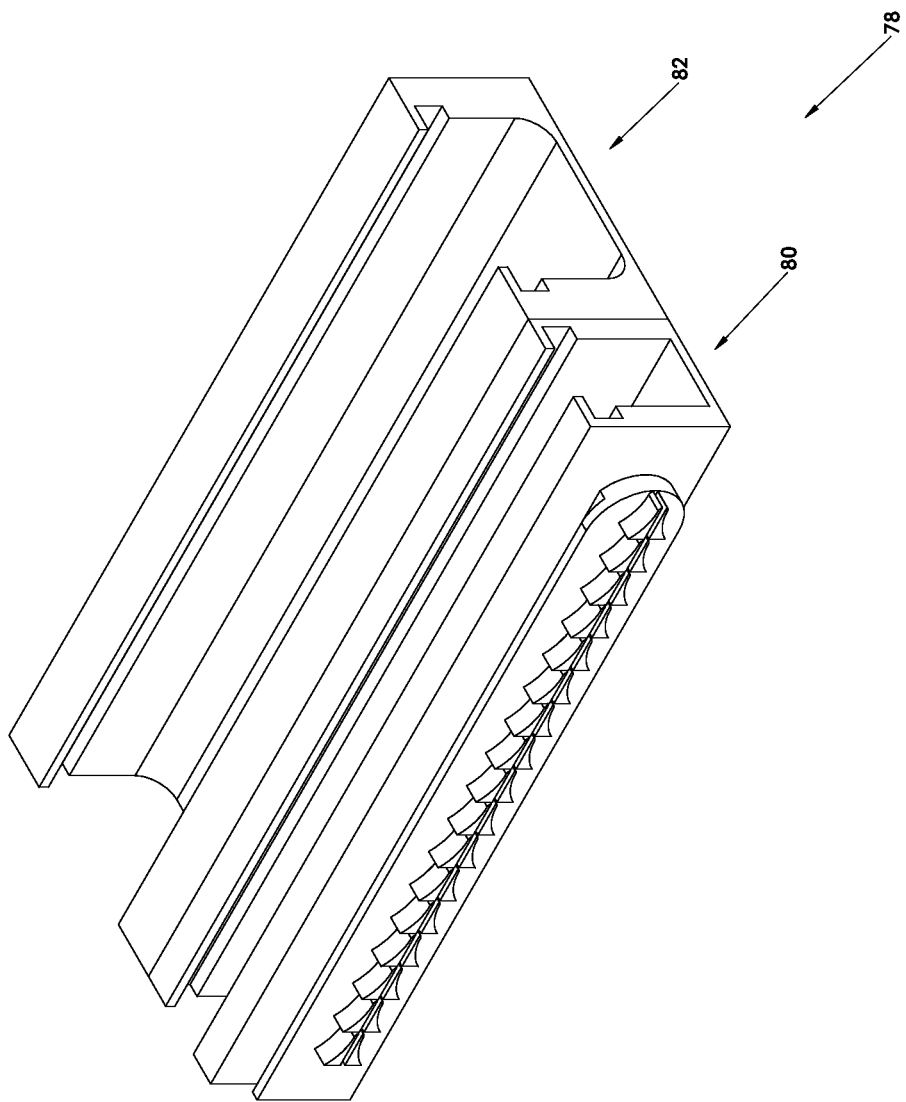

The modular applicator connector 78 is shown in FIGS. 7A and 7B. FIG. 7A shows the modular applicator connector 80 being inserted/connected/mounted to one side of a staple device connector 82. The applicator connector 80 may be attached to either side of the staple device connector 82. FIG. 7A shows On a portion of a male attachment 84 having a row 86 of flexible triangles 88 mounted on the applicator connector 80 vertical side 90. The other portion of a female attachment 92 being the complement of the male attachment 84 is shown. Both sides 94, 96 of the staple device connector 82 have the female attachments 92 so that the applicator connector 80 may be mounted to either side as required during surgery. The modular connector 78 in FIG. 7B shows the applicator connector 80 fully inserted onto the device connector 82.

The staple delivery applicator 10 further includes radiation shielding in either the staple cartridge 52 itself or on the applicator connector 58, preferably in the applicator cartridge 52 since the radioactive staples would be mounted there. The shielding material may be a part of the composition of the cartridge 52 or be a layer of shielding mounted thereabout. The anvil 61 of the cartridge unit 14 may also be shielded to fully prevent exposure from radiation to the operators of the staple applicator 10. The shielding would minimize the radiation dose to the physician deploying the device as well as to the other personnel in the operating room. The shielding will permit safe storage of this device in the Operating Room until it is time for use. The device will also be designed for sterilization, and resterilization, using steam, ethylene oxide and gamma radiation to provide total flexibility to the hospital.

Since any modifications, variations, and changes in detail can be made to the described embodiments of the invention, it is intended that all matters in the foregoing description and shown in the accompanying drawings be interpreted as illustrative and not in a limiting sense. Thus, the scope of the invention should be determined by the appended claims and their legal equivalents.

[i] Jemal, Siegel, et al. "Cancer Statistics, 2009." CA Cancer J Clin. 2009;59:225-249.

[ii] American College of Surgeons. "National Cancer Database for 2003." <http://www.facs.org/cancer/ncdb/index.html>.

[iii] Ginsberg, R. J. and L. V. Rubinstein. "Randomized Tidal of Lobectomy Versus Limited Resection for T1 N0 Non-Small Cell Luna Cancer." Lung Cancer Study Group Ann Thorac Surg. 1995 September; 60(3):615-22. <http://ats.ctsnetjournals.org/cgi/content/full/60/3/615>.

[iv] Martini, Pains, et al. "Incidence of Local Recurrence and Second Primary Tumors in Resented Stage I Lung Cancer." J Thorac Cardiovasc Surg. 1995 January;109(1):120-9

[v] Ichinose, Yano, et al. "The Correlation Between Tumor Size and Lymphatic Vessel Invasion in Resented Peripheral Stage I Non-Small-Cell Lung Cancer." A potential risk of limited resection. J Thorac Cardiovasc Surg. 1994 October;108(4):684-6.

[vi] Choi, N. C. "Prospective Prediction of Postradiotherapy Pulmonary Function. With Regional Pulmonary Function Data: Promise and Pitfalls." Int J Radiat Oncol Biol Phys. 1988 July;15(1):245-7.

[vii] Landreneau, Sugarbaker, et al. "Wedge Resection Versus Lobectomy for Stage I (T1 N0 M0) Non-Small-Cell Lung Cancer." J Thorac Cardiovasc Surg. 1997 April;113(4): 691-8; discussion 698-700.

[viii] Warren, W. H. and L. P. Faber. "Segmentectomy Versus Lobectomy in Patients With Stage I Pulmonary Carcinoma." Five-Year Survival and Patterns of Intrathoracic Recurrence. J Thorac Cardiovasc Surg. 1994 April;107(4): 1087-93.

[ix] Kodama, Doi, et. al. "Intentional Limited Resection for Selected Patients With T1 N0 M0 Non-Small-Cell Luna Cancer: A Single-Institution Study." J Thorac Cardiovasc Surg. 1997 September;114(3):347-53.

[x] Miller, J. I. and C. R. Hatcher, Jr. "Limited Resection. of Bronchogenic Carcinoma in the Patient With Marked Impairment of Pulmonary Function." Ann Thorac Surg. 1987 October;44(4):340-3.

[xi] Hilaris, B. S. and D. Nori. "The Role of External Radiation and Brachytherapy in Unresectable Non-Small Cell Lung Cancer." Surg Clin. North Am. 1987 October;67(5):1061-71.

[xii] Fleischman, Kagan, et al. "Iodine125 Interstitial Brachytherapy in the Treatment of Carcinoma of the Lung." J Surg Cocci. 1992 January;49(1):25-8.

[xiii] National Cancer Institute. "Phase III Randomized Study of Sublobar Resection. With Versus Without intraoperative Brachytherapy in High-Risk Patients With Stage I Non-Small Cell Lung Cancer." Protocol ID NCT00107172, ACDSOG-Z4032 SRCI. <http://www.cancer.gov/clinical-trials/ACOSOG-Z4032>.

[xiv] Lee, Daly, et al. "Limited Resection for Non-Small Cell Lung Cancer: Observed Local Control With Implantation of $^{125}$I Brachytherapy Seeds." Ann Thorac Surg. 2003 January;75(1):237-42.

[xv] Chen, Galloway, et al. "Intraoperative $^{125}$I Brachytherapy for High-Risk Stage I Non-Small Cell Lung Carcinoma." Int J Radiat Oncol Biol Phys. 1999 July 15;44(5):1057-63.

[xvi] Pisch, Beisley, et al. "Placement of $^{125}$I Implants With the Da Vinci Robotic System After Video-Assisted Thoracoscopic Wedge Resection: A Feasibility Study." Int J Radiat Oncol Biol Phys. 2004 Nov. 1;60(3):928-32.

What is claimed is:

1. A staple delivery applicator for delivering radioactive source staples during a medical treatment, said staple delivery applicator comprising:

an actuating means, said actuating means for controlling crimping of the source staples located distally from said actuating means, wherein a trigger device comprises:
- a hand holding section, a lever mounted in said hand holding section;
- a control section, said control section having one or more controls therein for crimping staples located distally from said trigger device, said control section having a control for closing an anvil of a source cartridge holder and for firing of source staples in a source staple cartridge therein to cause the staples to crimp, and a control for opening the anvil and releasing said trigger device, the lever being pivotally mounted to a reversible gear and operatively connected to a control cable within an actuator arm for controlling said source cartridge holder; and
- an actuator arm mounting section; said actuating means being removably attachable to said actuator arm on a proximal end; and
- a modular connector with two modular units, one modular unit being adapted to removably hold said source cartridge holder, the other modular unit being adapted to removably hold a surgical staple cartridge holder, said units being removably mounted together in said modular connector when in use, said source cartridge holder operatively attached to said actuator arm on a distal end and adapted to removably mount therein said source staple cartridge;
- wherein said actuating means is adapted for closing the anvil of said source cartridge holder and for firing of the source staples in said source staple cartridge therein to cause the staples to crimp, and opening and closing of the anvil by movement of the control cable.

2. The staple delivery applicator as recited in claim 1, wherein said modular unit for said cartridge holder may be mounted to either side of the modular unit for holding said surgical staple cartridge holder.

3. The staple deliver applicator as recited in claim 2, wherein said modular connector further includes radiation shielding.

4. A staple delivery applicator for delivering radioactive source staples during medical treatment, said staple delivery applicator comprising:
- an actuating means, said actuating means for controlling crimping of the source staples located distally from said actuating means;
- an actuator arm, said actuating means being removably attachable to said actuator arm on a proximal end;
- a source cartridge holder, said source cartridge holder operatively attached to said actuator arm on a distal end and adapted to removably mount therein a source staple cartridge;
- a modular connector with two modular units, one modular unit being adapted to removably hold said source cartridge holder, the other modular unit being adapted to removably hold a surgical staple cartridge holder, said units being removably mounted together in said modular connector when in use,
- wherein said actuating means is adapted for closing an anvil of said source cartridge holder and for firing of source staples in said source staple cartridge therein to cause the staples to crimp, and opening and closing of the anvil.

5. The staple delivery applicator as recited in claim 4, wherein said modular unit for said source cartridge holder may be mounted to either side of the modular unit for holding said surgical staple cartridge holder.

6. The staple deliver applicator as recited in claim 4, wherein said modular connector further includes radiation shielding.

* * * * *